United States Patent [19]
Brückner et al.

[11] Patent Number: 5,698,205
[45] Date of Patent: Dec. 16, 1997

[54] PHOTOSTABILIZATION OF TITANIUM DIOXIDE SOLS

[75] Inventors: Hans-Dieter Brückner; Ulrike Hamann, both of Darmstadt; Andrea Heyland, Reichelsheim, all of Germany

[73] Assignee: Merck Patent Gesellschaft Mit Beschrankter Haftung, Darmstadt, Germany

[21] Appl. No.: 297,077

[22] Filed: Aug. 29, 1994

[30] Foreign Application Priority Data

Aug. 30, 1993 [DE] Germany .................. 43 29 129.5

[51] Int. Cl.$^6$ ................... A61K 7/42; B01J 13/00
[52] U.S. Cl. ............... 424/401; 252/313.1; 252/314; 252/363.5; 423/610; 423/612; 424/59; 424/70.9
[58] Field of Search ............... 252/313.1, 314, 252/363.5; 424/59, 70.9, 401; 423/610, 612

[56] References Cited

U.S. PATENT DOCUMENTS

| | | | |
|---|---|---|---|
| 2,147,533 | 2/1939 | Katzoff et al. | 252/313.1 X |
| 2,220,966 | 11/1940 | Krchma | 252/313.1 X |
| 3,442,678 | 5/1969 | Ross | 106/437 |
| 3,632,527 | 1/1972 | Alpert et al. | 423/610 X |
| 4,999,181 | 3/1991 | Klee et al. | 423/610 X |
| 5,049,309 | 9/1991 | Sakamoto et al. | 252/313.1 |
| 5,068,056 | 11/1991 | Robb | 252/313.1 |
| 5,340,567 | 8/1994 | Cole et al. | 424/59 |
| 5,389,361 | 2/1995 | Osterried et al. | 424/59 |
| 5,403,513 | 4/1995 | Sato et al. | 252/313.1 X |
| 5,453,267 | 9/1995 | Kemp et al. | 424/59 |

FOREIGN PATENT DOCUMENTS 0 518 175  12/1992  European Pat. Off. .

*Primary Examiner*—Richard D. Lovering
*Attorney, Agent, or Firm*—Millen, White, Zelano & Branigan, P.C.

[57] ABSTRACT

The present invention relates to neutral titanium dioxide sols which have been stabilized with hydroxycarboxylic acids or derivatives thereof and are treated with metal ions, inorganic anions, complexing agents and/or oxidizing agents to improve the photostability.

18 Claims, No Drawings

PHOTOSTABILIZATION OF TITANIUM DIOXIDE SOLS

SUMMARY OF THE INVENTION

The present invention relates to neutral titanium dioxide sols which have been stabilized with hydroxycarboxylic acids or derivatives thereof and are treated with metal ions, inorganic anions, complexing agents and/or oxidizing agents to improve the photostability.

Because of their good skin tolerance and their high absorption in the UV range, neutral titanium dioxide sols are suitable for cosmetic uses, and here in particular for sunscreen cosmetics.

However, as is known, titanium dioxide is photoactive and discolors under the action of light. The extent of this discoloration depends on the modification of the titanium dioxide, the mode of preparation, the after-treatment and purification and the particle size.

EP 0 518 175 and U.S. patent application Serial No. 07/898,586 (now U.S. Pat. No. 5,389,361) describe a neutral titanium dioxide sol which is stabilized by hydroxycarboxylic acids or derivatives thereof. The sol described there comprises very small sol particles and therefore has an extremely large surface area and reacts particularly sensitively to solar radiation. Since this sol is intended specifically for UV protection, the effect of discoloration by darkening manifests itself in particular in cosmetic formulations. The sol discolors reversibly by darkening in direct sunlight or under exposure to artificial light, especially if air is excluded. The rapid discoloration indicates that hydroxycarboxylic acid or derivatives thereof not only have a stabilizing effect on the titanium dioxide sol but also promote the reduction of $Ti^{4+}$ to $Ti^{3+}$.

An object of the present invention is to provide a neutral titanium dioxide sol which is distinguished by a high resistance to light even over a relatively long period of time.

Upon further study of the specification and appended claims, further objects and advantages of this invention will become apparent to those skilled in the art.

Surprisingly, it has now been found that neutral titanium dioxide sols are photostable if they comprise 5–40 mole % of a hydroxycarboxylic acid or derivatives thereof and 0.1–20 mole % of metal ions, inorganic anions, complexing agents and/or oxidizing agents. The mole % data here are based on the total $TiO_2$ content of the dried sol.

The neutral metal oxide sol contains 35–75% by weight, in particular 40–70% by weight, and especially 50–60% by weight, of titanium dioxide or titanium dioxide hydrates. The dispersion medium is an aqueous medium and the pH range is preferably 6–8.

The invention thus relates to a photostable titanium dioxide sol, which is characterized in that the neutral sol comprises 5–40 mole % of a hydroxycarboxylic acid or derivatives thereof and 0.1–20 mole % of metal ions, anions, complexing agents and/or oxidizing agents.

The invention furthermore relates to a process for the preparation of the sols according to the invention, which is characterized in that, before, during or after stabilization of the titanium dioxide sol with a hydroxycarboxylic acid or derivatives thereof, the sol having a pH of preferably about 6–8, an aqueous metal salt solution, inorganic anions, a complexing agent and/or an oxidizing agent is added and, if appropriate, the sol is dried.

The neutral titanium dioxide sol is prepared by a procedure analogous to that described in EP 0 518 175. Thus, an aqueous solution of a titanium salt, preferably $TiCl_4$, can be converted into the sol state, for example by hydrolysis, which can be induced by heating, and/or by acid peptization and/or by addition of a base or by electrolysis or also by other processes known to the expert. The sol particles have an average size of preferably about 5–200 nm, especially 5–100 nm, and in particular <20 nm. The stabilizers are then added to the sol. The individual components can be added in any desired sequence. The metal ions, inorganic ions, complexing agents and/or oxidizing agents can be added at the same time as, or before or after the addition of the hydroxycarboxylic acid or its derivatives. It has proved particularly advantageous to add the additional stabilizer at room temperature (e.g., 20°–25° C.) to the neutral sol which has already been stabilized with hydroxycarboxylic acid or its derivative.

Suitable hydroxycarboxylic acids and derivatives thereof preferably contain 2–12 C atoms, especially 2–8 C atoms. Further, the hydroxycarboxylic acids and derivatives preferably contain 1–6 hydroxy groups and 1–4 —COOH acid groups. The acids can contain aliphatic moieties, e.g., having 1–20 carbon atoms. In the aliphatic moieties, 1–4 double bonds can be present; however, saturated acids are preferred.

Suitable examples of hydroxycarboxylic acids are citric acid, tartaric acid, maleic acid, hydroxyacetic acid, mucic acid, lactic acid, glyceric acid and gluconic acid. Suitable hydroxycarboxylic acid derivatives include, in particular, the acid amides, such as monoalkylamides and dialkylamides (e.g., —CO—NHR and —CO—NRR' wherein R and R' are each, e.g., $C_{1-10}$-alkyl), and salts, such as alkali metal salts, alkaline earth salts and amine salts. Ester derivatives can also be used.

Hydroxycarboxylic acids which are suitable for the stabilization are, in particular, citric acid and tartaric acid and salts thereof. In contrast, experiments with ascorbic acid lead to an intense red discoloration of the sols.

Metal ions which can be added to the sol are all the metal ions known to the expert, in the form of their aqueous metal salt solutions, the concentration of the cations being 0.1–20 mole %, preferably 1–10 mole %, based on the $TiO_2$ content of the sol. Particularly suitable metal ions are $La^{2+}$, $Fe^{2+}$, $Fe^{3+}$, $Sn^{4+}$, $Zn^{2+}$, $Ce^{3+}$ an $Zn^{2+}$ and $Sn^{4+}$.

The anions used are water-soluble inorganic fluorides, iodates, nitrates and sulfates, preferably alkali metal and ammonium fluorides, such as, for example, $NaNO_3$, $NaIO_3$, $Na_2SO_4$, $NaF$, $KF$, $NH_4F$, $KHF_2$, $NaHF_2$, $NH_4HF_2$, $KIO_3$, $KNO_3$ or $K_2SO_4$. The concentration of the anions is 0.1–20 mole %, preferably 1–10 mole %, based on the $TiO_2$ content of the sol.

The discoloration of the sol is also prevented by addition of complexing agents, such as, for example, EDTA, or other chelating agents, such as nitrilotriacetic acid [Titriplex® I], 1,2-diaminocyclohexylene-dinitrilotetraacetic acid (=CDTA) [Titriplex® IV], diethylenetriaminopentaacetic acid (=DTPA) [Titriplex® V], N-(2-hydroxy-ethyl)-ethylenediamino-N,N,N-triacetic acid [Titriplex® VII] and tetraethylenetetraaminohexaacetic acid (=TTHA) [Titriplex® VIII].

The complexing agents are added in an amount of 0.1–20 mole %, preferably 1–10 mole %, based on the $TiO_2$ content of the sol.

Since the discoloration of the $TiO_2$ sol by darkening is evidently based on the reduction of $Ti^{4+}$ to $Ti^{3+}$, this can also be suppressed by suitable oxidizing agents. Inorganic peroxides, such as, for example, hydrogen peroxide, sodium perchlorate, potassium perchlorate, perborates or peroxodisulfate, which are employed in an amount of 0.1–20 mole %, preferably 1–10 mole %, in particular 5–10 mole %, based on the $TiO_2$ content of the sol, have proved to be particularly suitable.

The stabilization methods mentioned can additionally also be combined with one another, in which case the content of hydroxycarboxylic acid or derivatives thereof in the sol should be in the range of 5–40 mole %, preferably 10–25% by weight and in particular 10–20% by weight, and that of the other stabilizers in total should not be more than 20 mole %, preferably 1–10 mole %, based on the $TiO_2$ content of the sol.

During the addition of the stabilizers, the mixture is stirred and at the same time, or thereafter, the pH is kept constant at preferably 6–8 by addition of a base, such as, for example, NaOH, KOH, $Na_2CO_3$ or $K_2CO_3$. It is often expedient to carry out the precipitation of the sol in the presence of an alcohol, such as methanol, ethanol, propanol, iso-butanol, n-butanol, tert-butanol or cyclohexanol. Finally, the photostabilized neutral sol can be dried in vacuo, in a drying cabinet, in a microwave oven or by freeze- or spray-drying. For example, the neutral titanium dioxide sol can be freeze-dried at pressures of about $1×10^{-3}$ mbar with drying times of typically about 2–30 hours. Alternatively, the neutral titanium dioxide sol can be spray-dried. Commercial spray-drying plants can be used; the inlet temperature is usually about 200°–500° C. and, in particular, 200°–350° C., and the outlet temperature is typically about 50°–300° C., in particular 80°–220° C. Typical spray pressures are about 3–10 bar. However, the sol can also be incorporated into formulations without prior drying.

The transparent sol is obtained again by dissolving the resulting white powder in water. The properties of the titanium dioxide sol do not change as a result of the drying and subsequent dissolving of the powder in water or an aqueous solution.

The sol according to the invention can be used for diverse industrial and cosmetic uses. The use of the titanium dioxide sol in cosmetics, in particular as UV protection, is particularly preferred.

The cosmetic formulation can comprise cosmetic adjuvants, for example, thickening agents, softening agents, moistening agents, surface-active agents, preservatives, agents which prevent foam formulation, perfumes, waxes, lanolin, propellants, dyestuffs and/or pigments, which color the agent itself or the skin, and other ingredients usually used in cosmetics. An oil, wax or other fatty substance, a lower monoalcohol or a lower polyol or mixtures thereof can be used as solubilizing agents. Other preferred embodiments are oily lotions based on naturally occurring or synthetic Oils and waxes, lanolin, fatty acid ester, in particular triglycerides or fatty acids, or oily-alcoholic lotions based on a lower alcohol, such as ethanol, or on a glycol, such as propylene glycol, and/or fatty acid esters, such as triglycerides of fatty acids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 29 129.5, filed Jul. 27, 1993, are hereby incorporated by reference.

EXAMPLES

The following examples are intended to illustrate the invention without limiting it.

Example 1

1. Preparation of a neutral titanium dioxide sol stabilized with citric acid 1 l of water is brought to a pH of 1.5 at 5° C. by addition of 10% HCl. 250 ml of an aqueous $TiCl_4$ solution (400 g of $TICl_4$/l of water) are then added at 3°–7° C. at a metering rate of 2 ml/minute, while stirring vigorously. The pH is kept at 1.5 by simultaneous metering-in of an ion exchanger (ion exchanger II, Art. No. 4766, hydroxyl form from E. Merck, Darmstadt). The ion exchanger is removed by filtration (nylon filter). A 3–3.5% by weight titanium dioxide sol is obtained and can be concentrated to 10–15% by weight by evaporation in vacuo (30° C., pressure <20 mbar).

200 g of a 12.6% by weight titanium dioxide sol are stirred with a solution of 12.6 g of citric acid in 13 ml of water at a pH of 1.5. The viscous mixture thereby formed is brought to a pH of 6.7 with 32% sodium hydroxide solution, while cooling (ice/water), the solution becoming colorless. The resulting transparent sol is freeze-dried under 0.1 mbar for 20 hours.

2. Stabilization of the titanium dioxide sol with $Zn^{2+}$

A solution of 10 g of $ZnCl_2$ in 10 ml of water is added in the course of 1.5 hours, while stirring and at room temperature, to 1000 g of titanium dioxide sol which has been stabilized with citric acid and neutralized (100 g of $TiO_2$). During the addition of the zinc salt solution, the pH is kept constant at 6.7 with 32% sodium hydroxide solution. The transparent sol thus obtained is isolated as a dry powder, which can easily be dissolved again in water, by spray-drying.

Example 2

Stabilization with $F^-$

The procedure is analogous to Example 1, but instead of the $ZnCl_2$ solution, an NaF solution (2.6 g of NaF in 75 ml of water) is rapidly added to the sol as the stabilizer in the second step and the mixture is subsequently stirred for 1 hour, the pH rising only slightly.

Example 3

Stabilization with sodium peroxodisulfate

The procedure is analogous to Example 1, but in the second step, a solution of 1.0 g of sodium peroxodisulfate in 9 ml of water is added, while stirring, to 100 g of the titanium dioxide sol which has been stabilized with citric acid (10 g of $TiO_2$).

The mixture is subsequently stirred for one hour and the sol is precipitated with ethanol, filtered off with suction and freeze-dried.

Example 4

Stabilization with EDTA

A solution comprising 7 g of trisodium citrate dihydrate in 10.5 g of water is added, at room temperature and while stirring vigorously, to 80 g of titanium dioxide sol prepared by electrolysis (10 g of $TiO_2$). The white flocks which initially form dissolve again after a short time. 4.66 g of disodium EDTA (Titriplex dissolved in 20 g of 2.5% sodium hydroxide solution) are added to the solution, the mixture is subsequently stirred for 1 hour and the pH is brought to 6.7 by addition of 32% sodium hydroxide solution. The sol is precipitated by addition of 90 ml of 2-propanol, filtered off with suction, washed with propanol, sucked dry and dried in a drying cabinet at 40° C. for 24 hours.

Example 5

Stabilization with $SnCl_4$

A tin(IV) chloride solution (0.439 g of $SnCl_4 \cdot 5H_2O$ in 5 g of $H_2O$) is added at room temperature to 80 g of titanium dioxide sol prepared by electrolysis (10 g of $TiO_2$) and the mixture is subsequently stirred for 1 hour. A citrate solution (7 g of trisodium citrate dihydrate in 10.5 g of $H_2O$) is then added, the mixture is subsequently stirred for 15 minutes and the pH is then brought to 6.7 with sodium hydroxide solution (w=32%). Working up is carried out analogously to Example 4.

Example 6

Stabilization with $MnCl_2$ and EDTA

A manganese chloride solution (7.60 g of $MnCl_2$ in 10 g of $H_2O$) is added to 1000 g of titanium dioxide sol prepared by electrolysis (125 g of $TiO_2$). The mixture is stirred for 1 hour and a solution of 87.5 g of trisodium citrate dihydrate in 130 g of $H_2O$ is then added and the mixture is subsequently stirred for 15 minutes. After addition of a solution of 58.07 g of disodium EDTA in 250 g of 2.5% strength NaOH, the mixture is stirred for 1 hour. The pH is brought to 6.7 with 32% sodium hydroxide solution. Working up is carried out analogously to Example 4.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A titanium dioxide sol comprising:
    titanium dioxide sol particles,
    an aqueous dispersion medium,
    5–40 mole %, based on $TiO_2$ content of sol, of a hydroxycarboxylic acid or a salt, ester or amide thereof as a stabilizing agent, and
    0.1–20 mole %, based on $TiO_2$ content of sol, of a further stabilizing agent, wherein said further stabilizing agent is selected from the group consisting of $La^{2+}$, $Fe^{2+}$, $Fe^{3+}$, $Sn^{4+}$, $Zn^{2+}$, $Ce^{3+}$, $Mn^{2+}$, inorganic fluorides, inorganic iodates, inorganic nitrates, one or more complexing agents, one or more oxidizing agents, and combinations thereof,
    wherein said sol is photostable and neutral.

2. A photostable titanium dioxide sol according to claim 1, wherein said hydroxycarboxylic acid is citric acid or tartaric acid.

3. A photostable titanium dioxide sol according to claim 1, wherein said further stabilizing agent is selected from the group consisting of $La^{2+}$, $Zn^{2+}$, $Sn^{4+}$, $Mn^{2+}$, $Ce^{3+}$, $Fe^{2+}$ and $Fe^{3+}$.

4. A photostable titanium dioxide sol according to claim 1, wherein said further stabilizing agent is selected from the group consisting of [$F^-$, $IO^-_3$, $SO_4^{2+}$ and $NO_3^{2-}$] inorganic fluorides, inorganic iodates and inorganic nitrates.

5. A photostable titanium dioxide sol according to claim 1, wherein said further stabilizing agent is EDTA.

6. A photostable titanium dioxide sol according to claim 1, wherein said further stabilizing agent is a perchlorate or a peroxodisulfate.

7. A photostable titanium dioxide sol according to claim 1, wherein said hydroxycarboxylic acid is citric acid or tartaric acid; said complexing agent is EDTA; and said oxidizing agents are perchlorates and peroxodisulfates.

8. A titanium dioxide sol according to claim 1, wherein said oxidizing agents are hydrogen peroxide, perchlorates, perborates and peroxodisulfates.

9. A process for the preparation of a photostable titanium dioxide sol, said sol comprising titanium dioxide sol particles, and an aqueous dispersion medium, said process comprising:
    stabilizing said sol by adding 5–40 mole %, based on $TiO_2$ content of said sol, of a hydroxycarboxylic acid or a salt, ester or amide thereof as a stabilizing agent, and
    after stabilization of said sol with said hydroxycarboxylic acid or a salt, ester or amide thereof, said sol having a pH of 6–8, adding 0.1–20 mole %, based on $TiO_2$ content of said sol, of a further stabilizing agent selected from the group consisting of metal ions, anions, one or more complexing agents, one or more oxidizing agents, and combinations thereof.

10. A process for preparing a dried photostable titanium dioxide sol, comprising:
    drying a sol prepared according to claim 9, and further comprising drying said sol.

11. A process according to claim 10, further comprising precipitating said sol with an alcohol prior to drying.

12. A process for precipitating a photostable titanium dioxide sol comprising: adding an alcohol to a sol prepared according to claim 9.

13. In a cosmetic formulation containing a carrier and a titanium dioxide sol particle, the improvement wherein said formulation contains a titanium dioxide sol prepared according to claim 9.

14. A process according to claim 9, wherein said metal ions are $La^{2+}$, $Fe^{2+}$, $Fe^{3+}$, $Sn^{4+}$, $Zn^{2+}$, $Ce^{3+}$ and $Mn^{2+}$, and said anions are inorganic fluorides, inorganic iodates and inorganic nitrates.

15. A process according to claim 14, wherein said one or more complexing agents are EDTA, nitrilotriacetic acid, 1,2-diaminocyclohexylene-dinitrilotetraacetic acid, diethylenetriamine pentaacetic acid, N-(2-hydroxy-ethyl)-ethylenediamino-N,N,N-triacetic acid and tetraethylenetetraaminohexaacetic acid, and said one or more oxidizing agents are perchlorates and peroxodisulfates.

16. A process according to claim 9, wherein said oxidizing agents are hydrogen peroxide, perchlorates, perborates and peroxodisulfates.

17. A titanium dioxide sol comprising:
    titanium dioxide sol particles having a particle size of 5–200 nm,
    an aqueous dispersion medium,
    5–40 mole %, based on $TiO_2$ content of sol, of a stabilizing agent selected from the group consisting of hydroxy carboxylic acid having 1–6 hydroxy groups and 1–4—COOH groups, a monoalkyl amide thereof wherein the alkyl group has 1–10 C atoms, a dialkyl amide thereof wherein each, alkyl group has 1–10 C atoms, an alkali metal salt thereof, an alkaline earth salt thereof, and an amine salt thereof, and 0.1–20 mole %, based on $TiO_2$ content of sol, of a further stabilizing agent, wherein said further stabilizing agent is at least one metal ion, at least one anion, at least one complexing agent, at least one oxidizing agent, or combinations thereof, wherein said at least one metal ion is $La^{2+}$, $Zn^{2+}$, $Sn^{4+}$, $Mn^{2+}$, $Ce^{3+}$, $Fe^{2+}$, $Fe^{3+}$, or combinations thereof, wherein said at least one anion are an inorganic fluoride, an inorganic iodate, an inorganic nitrate or combinations thereof, wherein said at least one complexing agent is EDTA, nitrilotriacetic acid, 1,2-di-aminocyclohexylene- dinitrilotetraacetic acid, diethylenetriaminepentaacetic acid, N-(2-hydroxy-ethyl)-ethylenediamino-N,N,N-triacetic acid, tetraethylenetetraaminohexaacetic acid or combinations thereof, and wherein said at least one oxidizing agent is an inorganic peroxide or combinations thereof.

18. A titanium dioxide sol according to claim 17, wherein said at least one oxidizing agent is hydrogen peroxide, a perchlorate, a perborate, a peroxodisulfate or combinations thereof.

\* \* \* \* \*